United States Patent [19] [11] 4,361,598
Yoldas [45] Nov. 30, 1982

[54] POLYMERIZED SOLUTIONS FOR DEPOSITING OPTICAL OXIDE COATINGS

[75] Inventor: Bulent E. Yoldas, Churchill Borough, Pa.

[73] Assignee: Westinghouse Electric Corp., Pittsburgh, Pa.

[21] Appl. No.: 200,164

[22] Filed: Oct. 24, 1980

Related U.S. Application Data

[63] Continuation of Ser. No. 65,706, Aug. 10, 1979, abandoned, which is a continuation of Ser. No. 931,346, Aug. 8, 1978, abandoned.

[51] Int. Cl.³ ............................ C07F 7/28; C07F 7/02; C07F 9/00; B05D 1/18
[52] U.S. Cl. ................................. 427/74; 106/287.16; 106/287.17; 106/287.18; 106/287.19; 136/243; 427/106; 427/160; 427/162; 427/164; 427/372.2; 427/380; 427/397.7
[58] Field of Search ................. 427/74, 106, 160, 162, 427/372.2, 380, 397.7, 164; 106/287.16, 287.17, 287.18, 287.19

[56] References Cited

U.S. PATENT DOCUMENTS

| | | | |
|---|---|---|---|
| 2,584,905 | 2/1952 | Moulton et al. | 106/287 |
| 2,689,858 | 9/1954 | Boyd | 260/429 |
| 2,710,267 | 6/1955 | Boyd | 117/121 |
| 2,768,909 | 10/1956 | Haslam | 117/121 |
| 3,094,436 | 6/1963 | Schroder | 117/215 |
| 3,460,956 | 8/1969 | Dahle | 106/287 |
| 3,640,093 | 2/1972 | Levene et al. | 65/134 |
| 3,791,808 | 2/1974 | Thomas | 65/30 |
| 3,811,918 | 5/1974 | Levene | 117/47 |
| 3,941,719 | 3/1976 | Yoldas | 252/463 |

Primary Examiner—James R. Hoffman
Attorney, Agent, or Firm—R. D. Fuerle

[57] ABSTRACT

A clear solution is prepared by reacting metal alkoxide with a mixture of critical amounts of water and/or acid in an alcohol diluted medium. Alkoxides may be Ti-$(OR)_4$ or $Ta(OR)_5$, or another metal alkoxide such as $Si(OR)_4$ in admixture with these alkoxides. Acids may be HCl or $HNO_3$. Quarter wave inorganic optical coatings are deposited by applying the alkoxide solution to a substrate then heating the coating at over 350° C. The coatings reduce reflectivity on silicon solar cells. The index of refraction of the coating can be varied by several techniques, including altering the proportion of titanium and silicon in the coating firing temperature, firing atmosphere. Thicknesses of the coating can be controlled by varying the rpm in spin application, withdrawal rate in dipping application, by concentration of the solution, by the type of solvent or the degree of polymerization of the titanium complexes.

29 Claims, 9 Drawing Figures

POLYMERIZED SOLUTIONS FOR DEPOSITING OPTICAL OXIDE COATINGS

This is a continuation of application Ser. No. 065,706, filed Aug. 10, 1979 (now abandoned), which was a continuation of application Ser. No. 931,346, filed Aug. 8, 1978 (now abandoned).

BACKGROUND OF THE INVENTION

Due to the shortage of hydrocarbon fuels the importance of silicon solar cells as an energy source has increased greatly in the last few years. The efficiency of silicon in absorbing solar radiation, however, is only about 60%, the other 40% being reflected back into the atmosphere. The amount of light reflected can be reduced by coating the silicon with a material having an index of refraction between that of silicon and air according to Fresnel's equation:

$$R = \left( \frac{n_1^2 - n_0 n_2}{n_1^2 + n_0 n_2} \right)^2$$

where $n_0$ is the index of air, $n_1$ is the index of the coating, and $n_2$ is the index of the silicon.

Thus, for silicon, which has an index of about 4, the coating should have an index of about 2.0. (If the coating is applied on a slightly oxidized surface, the index may have to be adjusted.) This maximum reduction in the amount of light reflected is achieved at a coating thickness of one quarter of a wavelength.

Presently, it is known how to deposit coatings having specific indices of refraction. For example $TiO_2$ coatings have an index of 2.5 to 2.7, $Al_2O_3$ coatings have an index of 1.76, $SiO_2$ coatings of 1.55, etc. In addition to the fact that the indices of refraction of these coatings are not exactly 2 (or whatever index is needed), the chemical vapor deposition, vacuum deposition, and RF sputtering techniques for applying them are very expensive.

PRIOR ART

U.S. Pat. No. 2,584,905 to Moulton discloses the formation of high reflectivity coatings from alcohol solutions of $TiCl_4$. The index of refraction can be adjusted by varying the proportion of Ti to Si. Indices of refraction are obtained of only 1.45 to 1.7.

U.S. Pat. No. 2,689,858 to Boyd discloses reacting organic derivatives of orthotitanic acid in alcohol with water to prepare polymers. The upper limit on the amount of water used is 1.6 moles per mole of Ti and the coating is not heated at a high temperature.

U.S. Pat. No. 3,460,956 to Dahle discloses the hydrolysis of tetra-alkyl titanates in alcohol to make coatings of $TiO_2$. The minimum amount of water used is 1.5 moles per mole of Ti. An organic acid is present in the solution.

U.S. Pat. Nos. 2,768,909 to Haslan and 2,710,267 to Boyd disclose hydrolyzing a titanium alkoxide in alcohol using atmospheric humidity.

U.S. Pat. No. 3,094,436 to Schroder discloses partially hydrolyzed esters of Ti and Si acid in alcohol. An anti-reflective coating is made and heat is used. A silica solution is made but not a titania solution. Humidity is used to obtain titania sols.

SUMMARY OF THE INVENTION

I have discovered how to make clear solutions which contain oxide constituents in a soluble polymerized form and from which uniform and continuous glass-like oxide films can be deposited on substrates at relatively low temperatures. From these solutions quarterwave anti-reflective (AR) coatings of desired thickness and refractive index can be deposited on photovoltaic cells and on other substrates. The solutions are made of a metal alkoxide, an alcohol, and water by a partial hydrolysis and polymerization process. They are applied to the substrate by any liquid application methods such as dipping or spraying, and the solvent and organics are evaporated. After a low temperature baking, the coating converts to a transparent, continuous oxide film tenaciously bonded on the substrate. The optical quality of the films are equivalent or better than the presently used more expensive methods such as vacuum deposition.

I have also found that I can vary the index of refraction of the coating continuously from 1.4 to 2.4 by using mixtures of alkoxides and by controlling processing variables, thus permitting fine-tuning of the index for AR coatings on different substrates and for specific wavelength of light. Also, a coating which is anti-reflective over a broad band can be made by making the coating with two layers of different indexes or materials processed differently.

The solution and coatings of this invention are optically clear and have about the same physical properties as coatings deposited by prior techniques, but when optimum approach nearly the maximum reduction in reflectivity that is theoretically possible.

The coating techniques of this invention are well suited for continuous mass production of AR coating at a fraction of the cost of prior techniques. Existing process for coating solar cells cost about 20 cents a watt; this process would cost one-half to one cent per watt at present prices.

Figure 1:
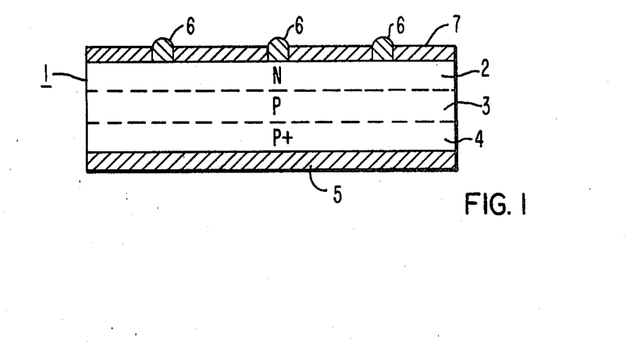
FIG. 1 is an isometric view in section of a certain presently preferred embodiment of a solar cell according to the invention.

In FIG. 1, a silicon wafer 1 is composed of an N layer 2, a P layer 3, and a P+ layer 4 from which electricity is drawn by grids 5 and 6 attached thereto respectively. On the surface of wafer 1 which is exposed to light is a coating 7 about ¼ wavelength thick according to this invention. The coating reduces the reflection of light back to its source and thereby enhances the efficiency of the solar cell. The captured light causes electrons to move from the N layer to the P+ layer thereby generating an electric current.

The coating shown in FIG. 1 is deposited from a solution derived from metal alkoxides. Alkoxides useful in this invention have the general formula $M(OR)_n$. In the formula, "M" represents a metal ion. This ion is preferably titanium as it is commercially the most important but it can also be tantalum. Lesser amounts of other alkoxides can be included as dopants to alter the index of refraction of the coating. For example, up to 25% (by weight) of the M ion content can be silicon or up to 15% (by weight) of the M ion content can be another M ion that forms a compatible alkoxide, such as boron, aluminum, zirconium. The small "n" in the formula is the valence of the M ion and can vary from 3 to 5. The R group is alkyl from $C_1$ to $C_6$. Each R group may be independently selected if desired though they are usually the same. The R group is preferably ethyl, isopropyl, or butyl because these alkoxides are commercially available and inexpensive. Also, the alcohols which are formed from there alkyl groups mix with water in the range of the invention.

The alcohols used in preparing the coating solutions can be any liquid alcohol, although ethanol is preferred as it is inexpensive. Higher alcohols produce thicker films. The alcohol need not be the same alcohol that is produced by the hydrolysis of the alkoxide, and in some instances it is desirable that they be different in order to obtain different viscosities. The amount of alcohol used should be sufficient to produce a solution having a solids content of about 0.1 to about 15% by weight based on equivalent $TiO_2$. A greater solids content for the same degree of hydrolysis will cause the solution to gel and a lesser solids content results in undesirably thin coatings. A preferred solids content is about 2 to about 8% by weight based on equivalent $TiO_2$. Stated another way, the preferred maximum is about 1 mole alkoxide per liter of final solution.

Metal-alkoxides, in general, hydrolyze quite vigorously when brought into contact with water forming oxides and hydroxides as represented by reactions.

$$M(OR)_n + nH_2O \rightarrow M(OH)_n + nR(OH) \qquad (1)$$

$$M(OR)_n + n/2 H_2O \rightarrow MO_{n/2} + nROH \qquad (2)$$

Whether the oxide or the hydroxide forms during the hydrolysis depends on the nature of the alkoxide. In either case, however, the resultant material is particulate, precipitates out, and therefore is not useful for coating. The alkoxides of titanium and tantalum, particularly, form precipitates even under insufficient water hydrolysis, and the formation of precipitates cannot be prevented under normal conditions. However, I have found a method of preparing soluble intermediate species from these alkoxides which are capable of polymerizing into an oxide network. Precipitate formation and self-condensation which would normally occur during the hydrolysis of these alkoxides are prevented from occurring by a careful control of molecular interaction during the hydrolysis where certain amounts of (OR) groups are left in the molecular structure. This is done by controlling first, the amount of water and dilution of the system, and second, by the presence of a critical amount of certain acids.

Because the water and/or alkoxide is diluted by the alcohol, the interaction of alkoxide and water molecules are reduced to a critical minimum where the complete hydrolysis of an alkoxide molecule cannot take place, occurrence of which would precipitate $TiO_2$. The first reaction produces a partially hydrolyzed alkoxide which does not precipitate:

$$Ti(OR)_4 + H_2O \rightarrow Ti(OR)_3OH$$

The partially hydrolyzed alkoxide molecules include $Ti(OR)_2(OH)_2$ and, $Ti(OR)(OH)_3$ and can then form a polymer with other alkoxide molecules.

$$(RO)_3Ti-OH + RO-Ti(OR)_3 \rightarrow (RO)_3Ti-O-Ti(OR)_3 + ROH$$

which can again react with other partially hydrolized titanium species. Because of the alkyl groups in the polymer it remains soluble in the alcohol. To keep the polymer soluble, it is necessary that not all the alkoxide bonds be hydrolyzed. Thus, the amount of water added is absolutely critical. If the amount is less than 1.7 moles of water per mole of alkoxide the coatings may be permanently cloudy and if more than 4 moles of water per mole of alkoxide is used, the solution will gel fairly quickly. Preferably, the amount of water should be 1.8 to 2.2 moles per mole of alkoxide.

In preparing the solution it is important to avoid contacting alkoxide with water without diluting one or both of them with alcohol first for otherwise a precipitate will form at the point of contact. Although either or both the water and alkoxide can be diluted with alcohol first, it is preferable to dilute the water, then to mix the water-alcohol mixture with the alkoxide. There should be a minimum of 600 cc. of alcohol used per mole of alkoxide; the preferable diluting range however is 2 to 8 liters of alcohol per mole of alkoxide.

When water and the alkoxide are brought into contact in an alcohol diluted system, the system turns cloudy. I have found that this cloudiness, which indicates condensation of separate particles, can be totally avoided by introducing at least 0.014 moles of either $HNO_3$ or HCl acids as heretofore described. If the introduction of acid is made into the water-alcohol solution before mixing with the alkoxide no cloudiness ever occurs, and this is therefore the preferred method of introducing the acid. Acid can be added anytime after the mixing occurs and it will cause the cloudy slurry to turn into a clear solution. However, if more than 0.2 moles of acid are used per mole of alkoxide, the solubility of the solution is reduced and it will turn cloudy after several days. So far, no organic acids have been found which work, and the only inorganic mineral acids which have been found to work are hydrochloric acid and nitric acid, although not all acids have been tried.

The solution, once prepared, should be aged for a few hours to permit the polymerization to proceed and stabilize. The solution should be clear at this stage. A clear solution indicates that a single continuous phase has been made rather than a particulate suspension or a precipitate. (A gel cannot be dissolved by adding solvent. To make a coating from the solution, it is first applied to a substrate. Application may be by spraying, painting, spinning, or other suitable method but dipping is the preferred method as it is most easily adapted to mass production.

For an anti-reflective coating on a solar cell, the substrate is usually silicon either in the form of wafers or as a continuous strip. Since silicon solar cells are most sensitive at a wavelength of about 6,000 Å, a one-fourth wavelength thick coating should be about 600 to about 750 Å. Another application of the coating is as an infrared reflective coating for incandescent light bulbs. By coating the inside of the bulb the infrared light is reflected back inside the bulb which results in less electricity being used for a given light output. Other useful substrates include various glasses such as gallium arsenide or calgoginide glasses where the coating can reduce reflection.

Figure 3:
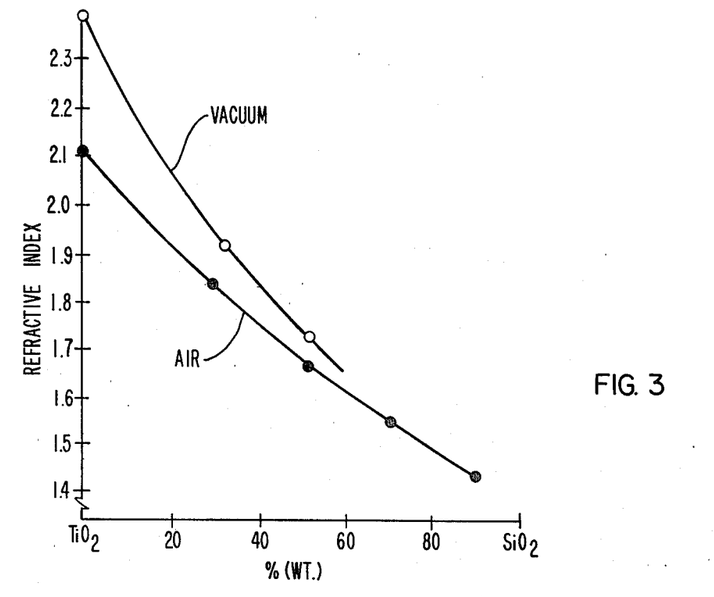

After the substrate has been coated, it is heated to at least 300° C. to drive off solvent and organics and form an inorganic metal oxide polymer. The film resulting after the heat treatment is continuous, has a uniform thickness within several Angstroms, and is tenaciously bonded onto the substrate. A temperature of 350° C. is needed to drive out remaining organic groups, but it may be desirable for some applications to leave some organics in the coating to lower the index of refraction as is illustrated in the examples. If the material is heated above about 600° C., it tends to become crystalline rather than amorphous. If the $TiO_2$ film thus obtained is heat treated in air it will have an index of refraction around 2.2. However, if the treatment is done in vacuum the index of refraction will be around 2.4. Of course, an index of refraction ranging from 2.4 to all the way down to 1.4 can be obtained by doping the solution with another suitable material. Silicon alkoxides are suitable for this purpose. FIG. 3 gives the precise composition for any desired index between 2.4 and 1.4. The resulting clear coating has about the same physical properties as coatings formed by prior vacuum techniques, but its optical properties are superior because the best coatings reduce reflectivity to very nearly the maximum amount which is theoretically possible.

When a single coating is applied to a substrate, the reflectivity reduction occurs at a minimum wavelength. The minimum wavelength can be broadened to cover a wide range of wavelengths by coating the substrate with two layers of film having different indices. For silicon, the lower layer should have a index of about 2.4 and the top layer a index of about 1.4. The lower layer index of 2.4 can be obtained by coating with 100% $TiO_2$ in vacuum. The top layer index of 1.4 can be obtained by coating with a 90%–10% mixture of $SiO_2$ and $TiO_2$ in air. Both coatings should each be a quarter wavelength thick. Each layer is fired separately.

The following examples further illustrate this invention.

EXAMPLE 1

18 g of $H_2O$ and 0.7 g $HNO_3$ were mixed well into 1000 g of ethyl alcohol. To this 114 g (½ mole) titanium tetra-ethoxide $Ti(OC_2H_5)_4$ was gradually added. A clear solution resulted. This solution was allowed to stand several hours. A dendritic-web silicon ribbon having ½ inch width was immersed in it. This sample was then withdrawn from the solution at a rate of 40 cm/min and baked in air at 400° C. for a few minutes. A uniform antireflective film of titanium oxide having a thickness of 680 Å and refractive index of 2.12 was formed on the silicon ribbon.

EXAMPLE 2

18 g of $H_2O$ was mixed well into 1000 g of ethyl alcohol. To this 170 g (½ mole) titanium butoxide. $Ti(OC_4H_9)_4$ was added under stirring. Within a few minutes the entire solution turned cloudy. To this 0.9 g of 70% concentrated nitric acid was added (0.02 mole $HNO_3$ per mole of alkoxide) with stirring. The milky slurry became clear within minutes. This solution was then spin applied on Czochalski-type round silicon wafers 1¼" in diameter at 900 rpm. When these wafers were fired in air they had a coating with a refractive index slightly over 2.1 and a thickness around 640 Å. Similarly coated wafers heat treated in vacuum had a refractive index around 2.4.

EXAMPLE 3

0.36 g (0.02 moles) $H_2O$ was mixed into 27 g ethyl alcohol. Into this, 4.06 g tantalum alkoxide. $Ta(OC_2H_5)_5$ was introduced under mixing. A clear liquid resulted. After 10 minutes of standing at room temperature, this solution acquired a milky appearance. 1 drop of $HNO_3$ acid was introduced into the solution and mixed. The cloudy appearance disappeared. It contained 7% equivalent $Ta_2O_5$ by weight.

After 3 days of aging, the solution described above was applied on a silicon solar cell with a spin application at 2500 rpm. The coated cell was then baked at 400° C. for 5 minutes. The following test results show the performance of the cell before and after the coating.

|  | $I_{sc}$(ma) | $V_{oc}$(V) | Efficiency (%) |
| --- | --- | --- | --- |
| Before Coating: | 21.20 | 0.539 | 8.95 |
| After Coating: | 28.6 | 0.552 | 12.7 |

$I_{sc}$ = short circuit current
$V_{oc}$ = voltage (open circuit)

Increase in efficiency by coating = $\frac{12.7 - 8.9}{8.9}$ .42 = 42%.

EXAMPLE 4

Figure 2:
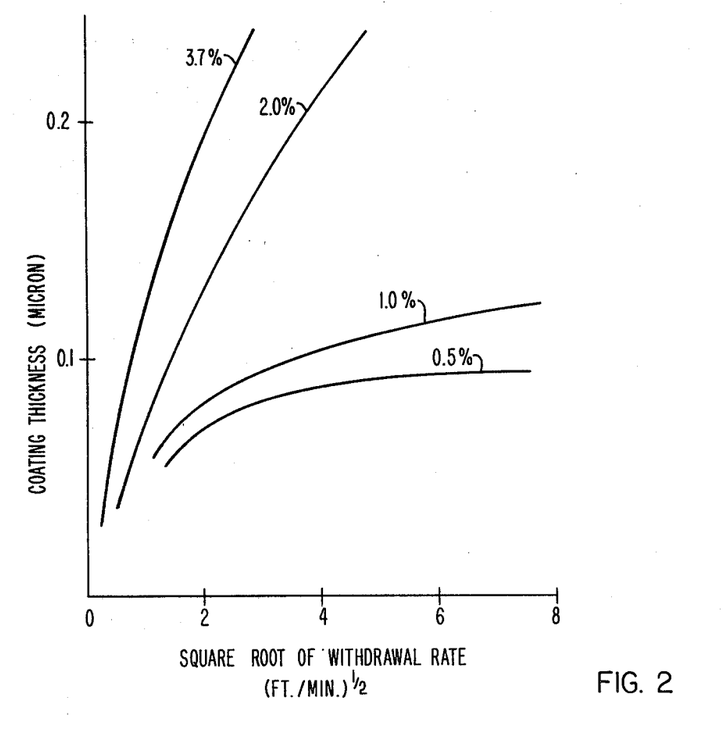
FIGS. 2 to 9 are graphs depicting experimental results described in the Examples.

15 g $H_2O$, 15 g silicon tetraethoxide $(Si(OC_2H_5)_4)$, and 0.6 g nitric acid were mixed into 853 g ethyl alcohol. Into this 116 g of titanium isopropoxide $(Ti(OC_3H_7)_4)$ was added gradually. A clear solution having 3.7 weight percent equivalent titania concentration resulted. Similarly, by using larger quantities of ethyl alcohol, solution having 0.5, 1.0, and 2.0 weight percent equivalent titania concentrations were also prepared. One-half inch wide 3 ft. long stainless steel ribbons were immersed in these solutions after 1 day aging. These samples were then withdrawn from the solutions at various speeds up to 64 ft/min. They were baked in air at 400° C. for 5 minutes. The coating thicknesses were then measured. FIG. 2 shows the effect of solution concentration and withdrawal rates on the thickness of films.

EXAMPLE 5

The following two solutions were prepared:

Solution A: 20.8 g silicon tetraethoxide, $Si(OC_2H_5)_4$ was mixed with 148 g ethyl alcohol. Precisely 1.8 g $H_2O$ was also added along with 1 drop of $HNO_3$ and the mixture was refluxed at 60° C. for several hours then set aside to cool. This gave a partially hydrolyzed silanol solution containing 3.5 wt.% equivalent $SiO_2$.

Solution B: 22.8 g $Ti(OC_2H_5)_4$ was added to 102 g ethyl alcohol. 3.5 g $H_2O$ and 4 drop of HCl acid were added to 100 g ethyl alcohol. These two preparations were mixed and aged several hours. The resultant liquid had a 3.5 wt.% equivalent $TiO_2$.

The two solutions were then mixed in various proportions and were permitted to age for several hours. The mixtures were deposited on silicon wafers by spinning at 1000 rpm and were heated in air and in vacuum at 500° C. to form coatings about 600 Å thick. FIG. 3 shows that the index of refraction depends on the proportion of $TiO_2$ to $SiO_2$ and on whether the coating was fired in air or in vacuum. A vacuum produces a denser coating having a higher index of refraction.

EXAMPLE 6

Figure 4:
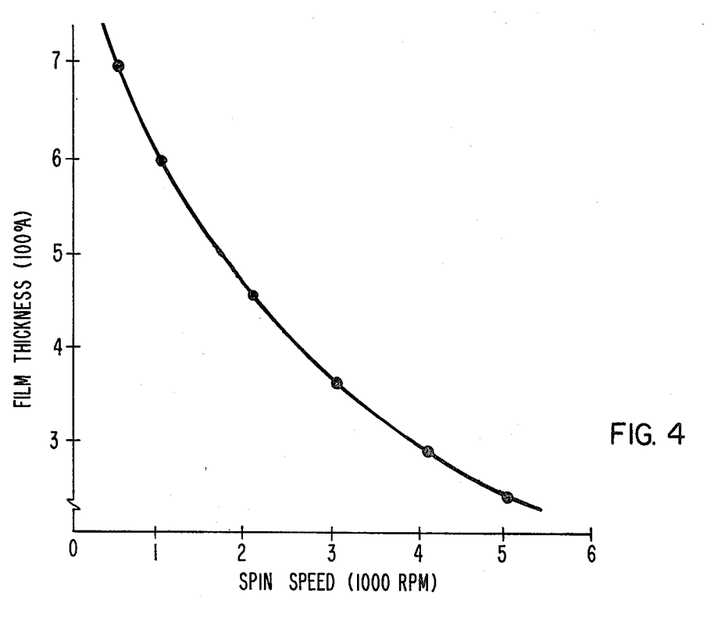

Example 5 was repeated except that Solution B contained 3.5 equivalent of $TiO_2$. The solution was placed on a silicon wafer and centrifuged at speeds ranging from 500 to 5,000 rpm before being at 500° C. FIG. 4 shows the effect of centrifuge speed on film thickness.

EXAMPLE 7

Figure 5:
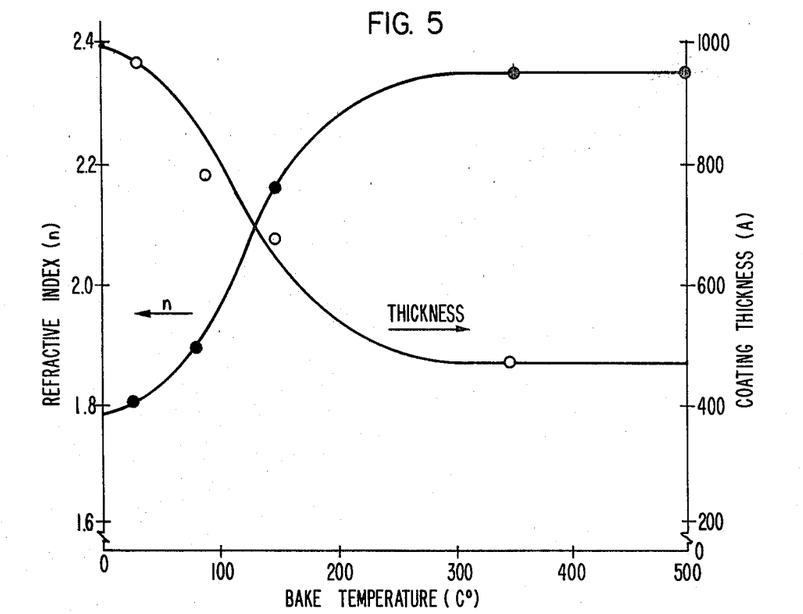
Figure 6:
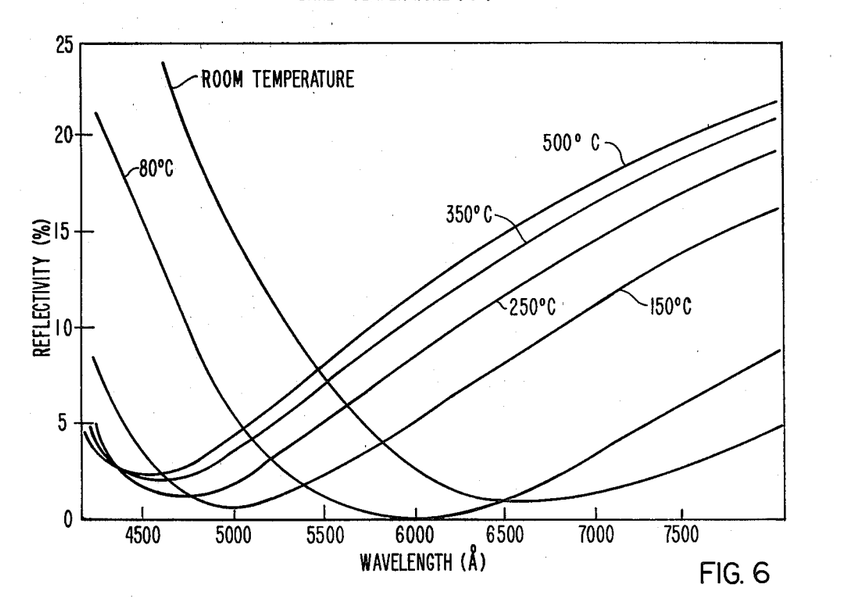

Example 6 was repeated at a centrifuge speed of 2000 rpm, except that the solutions were then baked at 250° C. to 500° C. FIG. 5 shows the effect that bake temperature has on film thickness and index of refraction. FIG. 6 shows the reflectivity of the surface films baked at various temperatures. It also shows how the minimum reflectivity can be shifted at various wavelengths with bake temperatures.

EXAMPLE 8

Figure 7:
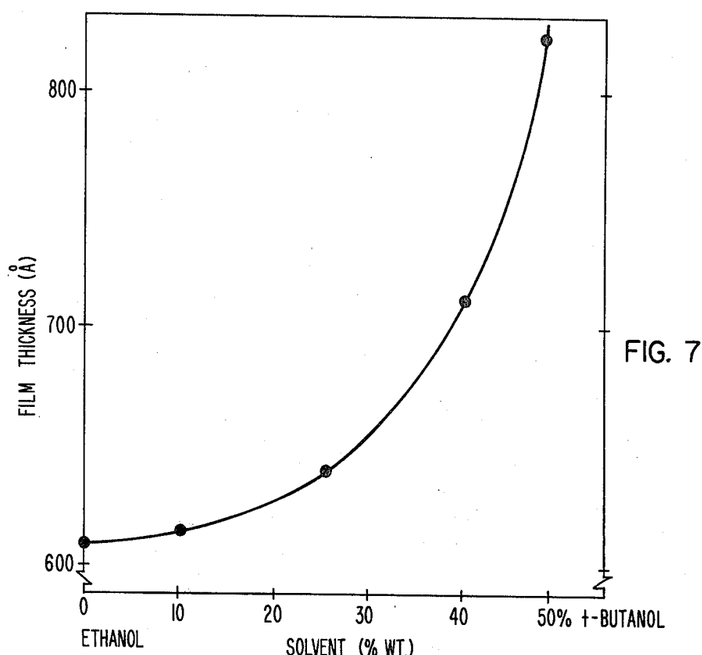

Example 6 was repeated except that the solution was 3.0% equivalent $TiO_2$ (2 moles $H_2O$), the alcohol was a mixture of ethanol and tertiary butanol, and the wafer was spum at 2,000 rpm. FIG. 7 shows the effect on film thickness of various proportions of ethanol and t-butanol. FIG. 7 shows that the thickness of the film can be controlled by the type of alcohol used.

EXAMPLE 9

Figure 8:
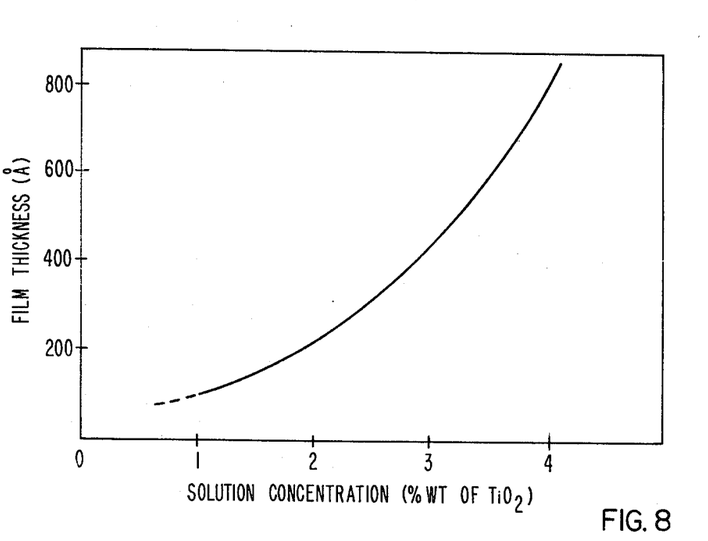

Example 6 was repeated using 2.5 moles of water per mole of $Ti(OC_2H_5)$ and controlling equivalent $TiO_2$ concentration by dilution with ethanol. Solutions were then coated on silicon wafers at 2000 rpm and baked at 500° C. FIG. 8 shows the relationship between solution concentration and film thickness. This gives another method of controlling film thickness.

EXAMPLE 10

P+ back surface field silicon solar cells having active areas slightly over 1 cm² were employed for anti-reflective testing. The silica and titania solutions were prepared as described in Example 5. These solutions were mixed to prepare a third solution to coat an oxide film with an index of 2 as indicated by FIG. 3 which requires 88% of $TiO_2$ and 12% of $SiO_2$. The fine tuning of the coating thickness is done by varying the rpm in spin application and the drawing speed in the dipping application. The solutions used required a spin speed of 800–1,000 rpm. The dipping was done by immersing the entire sample into the coating liquid and pulling it out at a continuous speed. It was found that extremely uniform anti-reflective coatings are deposited at a pulling rate 1–2 ft/min. It also appears to be feasible to increase this speed an order of magnitude or more by using diluted solutions. The following table gives the results.

| Solar Cell | I*$_{sc}$ (mA) Uncoated | I*$_{sc}$ (mA) Coated | Efficiency Uncoated | (%)*** Coated | Improvement |
|---|---|---|---|---|---|
| A | 21.10 | 29.40 | 8.56 | 12.24 | 43% |
| B | 21.60 | 31.00 | 9.37 | 13.34 | 42% |
| C | 21.40 | 30.50 | 9.03 | 12.91 | 43% |
| D | 20.80 | 28.90 | 8.65 | 12.82 | 48% |
| E | 22.00 | 30.50 | 9.43 | 14.04 | 49% |

\* = Short circuit current
\*\*\* = Calculation of efficiency takes into account changes in open circuit voltage and fill factor which are relatively insensitive to AR coating and therefore not given here seperately.

The E cell was a doubly-coated cell with films of two different indices. The rest of the cells are coated with single anti-reflective film with an index of 2. As shown, these cells showed as much as 48% increase in the efficiency.

From a purely theoretical point of view, if the reflection were to be eliminated entirely, there would be about 60% more energy available to the device over the uncoated state (38/62=60%). However this sixty percent is unattainable as an increase in device electrical output for several reasons. First, the zero reflectivity occurs only at one wavelength, not throughout the entire spectrum. Secondly, the response of the silicon device varies with the wavelength; therefore, it will not respond to all of the energy gain. For these reasons, the actual limit on potential efficiency increase with an anti-reflective coating is estimated to be about 50%. The 48 to 49% increase in efficiencies recently attained in this work appears to approach this limit.

EXAMPLE 11

Single coatings produce minimum reflectivity at a wavelength given by $\lambda = 4n_c t_c$ where $n_c$ and $t_c$ are the index and thickness of the coating respectively. All other wavelengths, however, are reflected with increasing intensity as they deviate from this value. Since in photovoltaic silicon cells the energy conversion takes place in the range of wavelengths covering approximately the solar spectrum, it is highly desirable to produce coatings whose antireflective characteristics also cover the entire range of solar spectrum.

It has been demonstrated that quarterwave double AR coatings can also be deposited by the technique of this invention.

A silicon wafer was initially coated with a quarter wave thick $TiO_2$ film fired in vacuum and having an index of 2.4. The solution used was similar to that of Example 1. Then a second quarter wave film having a composition of 90% $SiO_2$-10% $TiO_2$ was deposited from a solution prepared similarly to Example 5. As predicted by FIG. 3 this second coating had a refractive index of 1.4.

Figure 9:
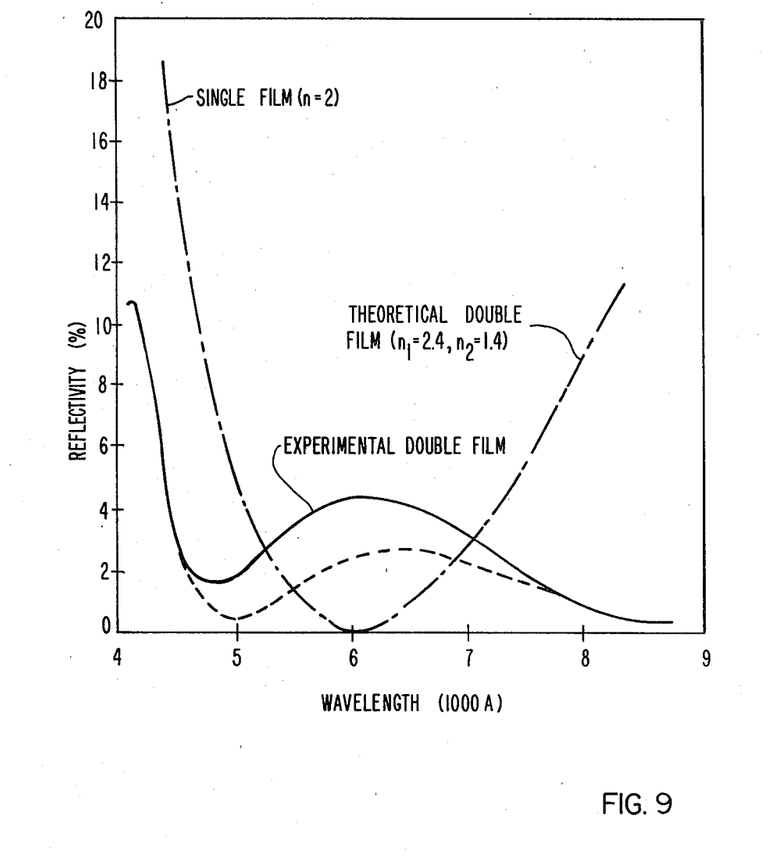

The combined reflectivity of this double film is shown in FIG. 9. As was predicted, a wide spectrum of antireflectivity was obtained. The total reflectivity as integrated over the 4500 Å to 900 Å range was less than 3% (uncoated silicon surfaces reflect about 40% in this range). A solar cell coated with double film showed 49% improvement in efficiency (see "solar cell E" in example 10).

What is claimed is:
1. A clear stable solution which comprises:
   (A) alkoxide having the general formula $M(OR)_n$ where M is selected from the group consisting of 0 to 100% Ti, 0 to 25% Si, 0 to 100% Ta, and up to 15% of a metal ion which forms an alkoxide, R is alkyl from $C_1$ to $C_6$, and n is the valence of M;
   (B) about 1.7 to about 4 moles of water per mole of alkoxide;
   (C) sufficient alcohol to give a solids content of about 0.1 to about 15% by weight based on equivalent oxide; and
   (D) a sufficient amount of a suitable acid to prevent cloudiness.
2. A solution according to claim 1 wherein the solids content is about 2 to about 8% by weight based on equivalent oxide.
3. A solution according to claim 1 which includes about 0.014 to about 0.2 mole of acid per mole of alkoxide.
4. A solution according to claim 3 wherein said acid is selected from the group consisting of nitric acid, hydrochloric acid, and mixtures thereof.
5. A solution according to claim 1 wherein said alcohol is ethyl alcohol.

6. A solution according to claim 1 wherein R is selected from the group consisting of ethyl, isopropyl, butyl, and mixtures thereof.

7. A solution according to claim 1 wherein M is all Ti.

8. A solution according to claim 1 wherein M is a mixture of Ti and Si.

9. A solution according to claim 1 wherein the amount of water is 1.8 to 2.2 moles per mole of alkoxide.

10. A method of preparing an oxide coating on a substrate, said coating having a predetermined index of refraction between about 1.4 and about 2.4 comprising:
  (A) preparing a clear solution according to claim 1 wherein M is a 0 to 25% Si and the remainder Ti;
  (B) applying said clear solution to said substrate; and
  (C) heating said substrate to about 300° to about 600° C.

11. A method according to claim 10 wherein said substrate is heated in a vacuum.

12. A method according to claim 10 wherein said substrate is silicon.

13. A method according to claim 10 wherein said application is by dipping.

14. A method according to claim 10 wherein said method is applied twice to the same substrate so that a two-layered coating is produced.

15. A method according to claim 14 wherein the lower layer is $TiO_2$ fired in vacuum and the top layer is 90% $TiO_2$ and 10% $SiO_2$ fired in air, and each layer is a quarter wavelength in thickness.

16. A method of preparing a clear solution of a metal alkoxide comprising:
  (A) adding sufficient alcohol to give a final solids content of about 0.1 to about 15% by weight based on equivalent oxide to either or both of:
    (1) alkoxide having the general formula $M(OR)_n$ where M is selected from the group consisting of 0 to 100% Ti, 0 to 30% Si, 0 to 100% Ta, and up to 15% of another metal ion which forms an alkoxide, R is alkyl from $C_1$ to $C_6$, and n is the valence of M; and
    (2) about 1.7 to about 4 moles of water per mole of alkoxide;
  (B) mixing together said alkoxide and said water; and
  (C) adding a sufficient amount of a suitable acid to prevent cloudiness.

17. A method according to claim 16 wherein said alcohol is added entirely to said water.

18. A method according to claim 16 wherein titanium alkoxide is added to a mixture of said alcohol and partially hydrolyzed silicon alkoxide.

19. A method according to claim 16 wherein a mixture of alkoxides is used and each alkoxide is partially hydrolyzed before mixing.

20. A method according to claim 16 wherein said acid is added to a mixture of said water and said alcohol, which is then mixed with said alkoxide.

21. A method according to claim 16 wherein the amount of water is 1.8 to 2.2 moles per mole of alkoxide.

22. A method according to claim 16 wherein the solids content is about 2 to about 8% by weight based on equivalent oxide.

23. A method according to claim 16 wherein said acid is selected from the group consisting of nitric acid, hydrochloric acid, and mixtures thereof.

24. A method according to claim 16 wherein said water is diluted with said alcohol, which is then mixed with said alkoxide.

25. A method according to claim 16 wherein the amount of said acid is about 0.014 to about 0.2 moles per mole of alkoxide.

26. A method according to claim 16 wherein said solution is aged for several hours prior to use.

27. A method according to claim 16 wherein said solution is applied to a substrate by dipping said substrate into said solution.

28. A clear stable solution which comprises:
  (A) alkoxide having the general formula $M(OR)_n$ where at least 60% of M is selected from one of titanium and tantalum, up to 25% of M is silicon, and up to 15% of M is a metal which forms an alkoxide, each R is independently selected from $C_1$ to $C_6$, and n is the valence of each M;
  (B) about 1.7 to about 4 moles of water per mole of alkoxide;
  (C) sufficient alcohol to give a solids content of about 0.1 to about 15% by weight based on equivalent oxide; and
  (D) about 0.014 to about 0.2 moles of acid per mole of alkoxide.

29. A method of coating a substrate with a solid continuous layer of a metal oxide comprising:
  (1) preparing a clear stable solution which comprises:
    (A) alkoxide having the general formula $M(OR)_n$ where at least 60% of M is selected from one of titanium and tantalum, up to 25% of M is silicon, and up to 15% of M is a metal which forms an alkoxide, each R is independently selected from $C_1$ to $C_6$, and n is the valence of each M;
    (B) about 1.7 to about 4 moles of water per mole of alkoxide;
    (C) sufficient alcohol to give a solids content of about 0.1 to about 15% by weight based on equivalent oxide; and
    (D) about 0.014 to about 0.2 moles of acid per mole of alkoxide.
  (2) applying said clear stable solution to said substrate;
  (3) heating said substrate to about 300° to about 600° C.

* * * * *